United States Patent [19]

Grollier et al.

[11] 4,201,766
[45] May 6, 1980

[54] HAIR CONDITIONING COMPOSITION AND METHOD OF USING THE SAME

[75] Inventors: Jean-François Grollier; Chantal Fourcadier, both of Paris, France

[73] Assignee: L'Oreal, Paris, France

[21] Appl. No.: 881,512

[22] Filed: Feb. 27, 1978

[30] Foreign Application Priority Data

Mar. 2, 1977 [FR] France ................................ 77 06044

[51] Int. Cl.² ............................................. A61K 7/06
[52] U.S. Cl. ............................. 424/70; 260/29.6 HN; 424/DIG. 2; 424/71; 8/406
[58] Field of Search .................... 260/78 SC, 29.6 HN; 424/329, 70, 71, DIG. 2

[56] References Cited

U.S. PATENT DOCUMENTS

| | | | |
|---|---|---|---|
| 2,271,378 | 1/1942 | Searle | 424/329 |
| 2,882,185 | 4/1959 | Yalko et al. | 260/78 SC |
| 2,926,116 | 2/1960 | Keim | 260/78 SC |
| 2,926,154 | 2/1960 | Keim | 260/78 SC |
| 3,560,609 | 2/1971 | Korden | 424/71 X |
| 3,560,610 | 2/1971 | Korden | 424/71 X |
| 3,769,398 | 10/1973 | Hewitt | 424/70 |
| 3,912,808 | 10/1975 | Sokol | 424/71 |
| 3,917,817 | 11/1975 | Vanlerberghe et al. | 424/70 |

FOREIGN PATENT DOCUMENTS 1035296 7/1966 United Kingdom .

Primary Examiner—Joseph E. Evans
Assistant Examiner—Vera C. Clarke
Attorney, Agent, or Firm—Cushman, Darby & Cushman

[57] ABSTRACT

A cosmetic composition for the hair comprises in combination at least one crosslinked polyamino-amide and at least one cationic polymer having recurring units of the formula

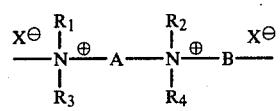

wherein
$R_3$ and $R_4$ each independently represent alkyl having 1–3 carbon atoms,
$R_1$ and $R_2$ each independently represent alkyl having 1–3 carbon atoms or hydroxy alkyl having 1–3 carbon atoms, or when $R_2=R_4=CH_3$ and $R_1=R_3$, $R_1$ and $R_3$ can represent alkyl having 4–8 carbon atoms, or when $R_2=R_4=R_1=CH_3$, $R_3$ can represent benzyl, cyclohexyl or alkyl having 4–12 carbon atoms,
$X^\ominus$ is an anion,
A and B each independently represent linear or branched alkylene having 2–20 carbon atoms in the chain, or A represents $-(CH_2)_n-Z-(CH_2)_n-$, $-CH_2-C_6H_4-CH_2-$ or $-CH_2-CH(OH)-CH_2-$, n being 2 or 3 and Z representing $-O-$ or $-NH-CO-NH-$.

19 Claims, No Drawings

HAIR CONDITIONING COMPOSITION AND METHOD OF USING THE SAME

The present invention relates to a new cosmetic composition for the hair and to a process for conditioning the hair using said composition.

It is known that hair generally is degraded, to varying degrees, by the action of atmospheric agents and also by the action of such cosmetic treatments such as bleaching, permanent waving and dyeing. As a result, the hair is often difficult to untangle and to style. It is even difficult on an abundant head of hair subjected to such treatments to maintain an acceptably appearing hair style because the hair lacks vigor and liveliness.

It has been proposed, in an effort to overcome these disadvantages, to apply to the hair "conditioning" agents which facilitate the untangling and combing of wet hair and which provide acceptable maintenance of a hair style, by imparting to dry hair body, fullness and elasticity.

Such known efforts include, principally, the use of certain crosslinked polyamino-polyamides which are described in Luxembourg Pat. No. 68,901 or in U.S. applications Ser. No. 528,577, filed Nov. 29, 1974, now abandoned, and Pending Ser. No. 762,804, filed Jan. 26, 1977.

These crosslinked polyamino-polyamides are very interesting hair conditioners. They impart to the hair the desirable properties of liveliness and fullness and they assure good maintenance of a hair style.

It has, however, been noted that the repeated application of these conditioning agents, while imparting fullness and elasticity to the hair and while assuring good maintenance of the hair style, imparts a harsh and grating feel to the hair and more particularly to the sensitive hair ends.

It has now been discovered that this undesirable effect can be avoided by using crosslinked polyamino-polyamides in combination with certain particular cationic agents, while at the same time preserving the conditioning effect of these polyamino-amides. Further, it has been found that the use of this combination of components has the effect of reinforcing the stability of the hair.

The particular cationic agents which are employed in accordance with the present invention, in combination with crosslinked polyamino-amides are polymers comprising recurring units of the following Formula I:

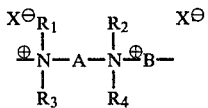

wherein
$R_3$ and $R_4$ each independently represent alkyl having 1–3 carbon atoms;
$R_1$ and $R_2$ each independently represent alkyl having 1–3 carbon atoms or hydroxyalkyl having 1–3 carbon atoms; or when $R_2=R_4=CH_3$ and $R_1=R_3$, $R_1$ and $R_3$ can additionally represent alkyl having 4–8 carbon atoms; or when $R_2=R_4=R_1=CH_3$, $R_3$ can additionally represent benzyl, cyclohexyl or alkyl having 4–12 carbon atoms;
$X^\ominus$ is an anion;
A and B each independently represent linear or branched alkylene having 2–20 carbon atoms in the chain, $-(CH_2)_n-Z-(CH_2)_n-$, $-CH_2-C_6H_4-CH_2-$ or $-CH_2-CH(OH)-CH_2-$ wherein n is a whole number equal to 2 or 3, and Z represents either $-O-$ or $-NH-CO-NH-$.

$X^\ominus$ is a cosmetically acceptable anion derived from an organic or inorganic acid, e.g. a halide (bromide, iodide or chloride) anion; or an anion derived from other inorganic acids such as phosphoric acid, sulfuric acid, etc . . . ; or an anion derived from a sulfonic or carboxylic acid, e.g. an alkanoic acid having 2–12 C atoms, such as acetic acid; a phenylalkanoic acid, such as phenylacetic acid; benzoic acid, lactic acid, citric acid; paratoluene sulfonic acid; etc . . .

The various crosslinked polyamino-amides used in the compositions of the invention are obtained by crosslinking a polyamino-amide resulting from the polycondensation of an acid derivative on a polyamine. These polyamino-amides are described in the above referred to Luxembourg patent and U.S. applications, the latter being incorporated herein by reference, as well as in the first certificate of addition, No. 77 06031 to French patent application No. 74.39242 filed Nov. 29, 1974, and entitled "Hair Conditioning Compositions" and in U.S. application Ser. No. 881,513, filed Feb. 27, 1978, which is a CIP of said Ser. No. 762,804, also incorporated herein by reference. The acid derivative is selected from the group consisting of organic dicarboxylic acids, ethylenically unsaturated aliphatic mono- and di-carboxylic acids, the esters of said acids, as well as mixtures thereof. The polyamine is selected, preferably, from bis-primary and mono- or bis-secondary polyalkylene polyamines. From 0–40 mole percent of the selected polyamine can be replaced by a bis-primary amine or a bis-secondary amine. A preferred bis-primary polyamine is ethylene diamine or hexamethylene diamine, and a preferred bis-secondary amine is piperazine.

The crosslinking reaction is preferably carried out using an agent selected from the group consisting of:
(a) epihalohydrins, diepoxides, dianhydrides, unsaturated anhydrides, bis-unsaturated derivatives, bis-halohydrins, bis-azetidiniums, bis-haloacyl diamines and alkyl bis-halides,
(b) oligomers obtained with the crosslinking agents in (a) above as well as
(c) products of the quaternization of crosslinking agents in (a) and (b) above, which have alkylatable tertiary amine groups.

The crosslinked polyamino-amides used in the compositions of the present invention have, preferably the following characteristics:
(i) they are obtained using 0.025 to 0.35 mole of crosslinking agent per amine group of the polyamino-amide, and generally by using less than 0.2 and in particular less than 0.1 mole of crosslinking agent per amine group of the polyamino-amide;
(ii) they are soluble in water up to 10 weight percent without the formation of a gel;
(iii) the viscosity of such a 10 weight percent solution in water at 25° C. is greater than 3 centipoises and is usually between 3 and 200 and more specially between 20 and 50 centipoises; and
(iv) they do not carry, preferably, any reactive groups and in particular they do not have any alkylating characteristics and they are chemically stable.

The acids useful for the preparation of these polyamino-amides are principally (1) saturated organic dicarboxylic acids having 3–10 carbon atoms, and in particular 6 to 9 carbon atoms, such as for instance adipic acid, 2,2,4-trimethyl adipic acid, 2,4,4-trimethyl adipic acid, diglycolic acid and terephthalic acid; and (2) ethylenically unsaturated aliphatic mono- and di-carboxylic acids such as acrylic acid, methacrylic acid and itaconic acid. The esters of the above mentioned acids, for example, the methyl and ethyl esters thereof can also be employed. Further, mixtures of two or more of these acids and/or their esters can also be used.

The polyamines useful for the preparation of the polyamino-amides are principally those wherein the alkylene groups have 2–4 carbon atoms, such as, for example, diethylene triamine, dipropylene triamine, triethylene tetramine and mixtures thereof.

Generally, the molar ratio of the reactants, namely the polyamine and the acid derivative, is about 1, but a moderate excess of polyamine may be used. However, the molar ratio polyamine/acid derivative is, preferably, less than or equal to 1.2.

Moreover, up to 20 molar percent of hexamethylene diamine or up to 40 molar percent of ethylene diamine or piperazine per 100 moles of amine can be employed.

The preparation of the polyamino-amides useful in the compositions of the present invention is described (or is analogous to that described) in the Luxembourg patent and in the U.S. applications mentioned above. The polyamino-amides thus obtained are crosslinked by the addition of a crosslinking agent, such as epichlorhydrin, diglycidyl ether, N,N'-bis-epoxypropyl-piperazine, the dianhydride of butane tetracarboxylic acid, the dianhydride of pyromellic acid or bis-unsaturated derivatives, such as for example, divinyl sulfone and methylene bis-acrylamide, N,N'-bis-epoxypropyl piperazine quaternized, for example, with 1 or 2 moles of dimethyl sulfate, piperazine bis-acrylamide, a bis-unsaturated oligomer obtained by the action of an excess of piperazine bis-acrylamide on piperazine, a bis-halohydrin oligomer prepared by the reaction of an excess of epihalohydrin on piperazine and optional quaternization of the product obtained, for example, by dimethyl sulfate, 1,3-bis-piperazinyl-2-propanol quaternized by epichlorohydrin, piperazine bis-chloracetamide, piperazine bis-omega-bromo-undecanamide, bifunctional alkylating agents having the following Formula II:

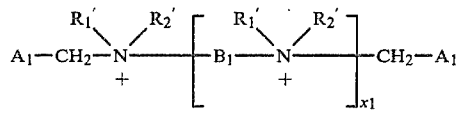

wherein
$x_1$ represents a whole number between 0 and 7;
$A_1$ represents

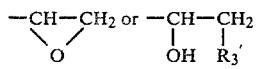

wherein $R'_3$ represents halogen and preferably chloride or bromide;
$R'_1$ and $R'_2$ represent lower alkyl or hydroxyalkyl, having 1–4 carbon atoms;
$B_1$ represents alkylene containing 2–6 carbon atoms,

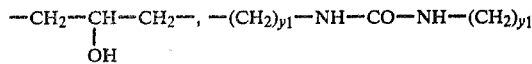

wherein $y_1$ is equal to a whole number from 1 to 4 and in particular those for which $A_1$ represents

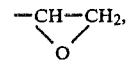

$R'_1$ and $R'_2$ represent lower alkyl and in particular methyl and $x_1$ is equal to 0, and bis-epoxypropyl dimethyl ammonium chloride.

The amount of crosslinking agent employed can vary depending on the particular polyamino-amide and of the cross-linking agent selected, and can easily be determined by adding the desired crosslinking agent to an aqueous solution of the selected polyamino-amide until the viscosity of a 10% solution at 25° C. is between 3 centipoises and the viscosity corresponding to the gel state, the crosslinked polyamino-amide remaining soluble in water.

In addition to crosslinked polyamino-amides described in the aforementioned Luxembourg patent, the Certificate of Addition to French Patent application No. 74 39242 and the said U.S. applications, those which are described in French Pat. No. 1,583,363 can also be employed in the present invention.

A preferred polymer of this type is an adipic acid-dialkylaminohydroxyalkyl-dialkylene triamine copolymer in which the alkyl moiety has 1–4 carbon atoms and represents preferably, methyl, ethyl and propyl. Particularly remarkable results are achieved employing adipic acid-dimethylamino-hydroxypropyl-diethylenetriamine copolymers sold under the name Cartaretine, F, F$_4$ or F$_8$ by Sandoz.

Other polymers which can also be employed in the present invention are those obtained by the reaction of a polyalkylene polyamine having two primary amine groups and at least one secondary amine group with a dicarboxylic acid selected from diglycolic acid and saturated aliphatic dicarboxylic acids having 3–8 carbon atoms, the molar ratio between the polyalkylene polyamine and the dicarboxylic acid being between 0.8:1 and 1.4:1. The resulting polyamide is then reacted with epichlorhydrin, in a molar ratio of epichlorohydrin relative to the secondary amine group of the polyamide between 0.5:1 and 1.8:1. These polymers are described in U.S. Pat. Nos. 3,227,615 and 2,961,347.

Particularly preferred polymers of this type are those sold under the name HERCOSETT 57 by Hercules Incorporated; and under the name PD 170 or DELSETTE 101 by Hercules in the case of a copolymer of adipic acid and epoxypropyl diethylene triamine.

Representative crosslinked polyamino-amides used in accordance with the present invention include (1) compound B$_1$, which is the compound described in Example Ia of Ser. No. 762,804. It is obtained by the polycondensation of an equimolar mixture of diethylenetriamine and adipic acid, followed by crosslinking with epichlorhydrin of the polymer obtained at a rate of 11 moles of epichlorhydrin per 100 amine groups;

(2) compound B$_2$ which is the compound described in Example Ib of Ser. No. 762,804. It is obtained by crosslinking the polycondensate of equimolar amounts of diethylenetriamine and adipic acid with methylene bis-acrylamide (12.1 moles per 100 amine groups of the polyamino-amide);

(3) compound $B_3$ which is the compound described in Example Ic of Ser. No. 762,804. It is obtained from the same polycondensate as in compound $B_2$, but it is crosslinked with N,N'-bis epoxy propyl piperazine, at a rate of 7.3 moles of crosslinking agent per 100 amine groups of the polyamino-amide;

(4) compound $B_4$ which is the compound described in Example IIIb of Ser. No. 762,804. It is obtained by the polycondensation of an equimolar mixture of triethylene tetramine and adipic acid, then crosslinked with methylene bis-acrylamide, at a rate of 3.4 moles of crosslinking agent per 100 amine groups of the polycondensate;

(5) compound $B_5$ which is the compound described in Example IVa of Ser. No. 762,804. It is obtained by the equimolar polycondensation of the reaction product of 2 moles of methyl itaconate with 1 mole of ethylenediamine and of diethylenetriamine. The polycondensate is then crosslinked with epichlorohydrin at a rate of 2.2 moles per 100 amine groups of the polycondensate;

(6) compound $B_6$ which is the compound described in

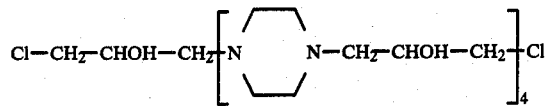

which is obtained by the reaction of epichlorohydrin and piperazine in molar amounts of 5:4. 8.5 moles of crosslinking agent per 100 amine groups of the polycondensate were used;

(12) compound $B_{12}$ is obtained from the same polycondensate as for $B_1$ which is then crosslinked with a material of the formula

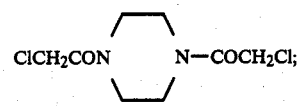

(13) compound $B_{13}$ is obtained from the same polycondensate as $B_1$, which is then crosslinked with a material of the formula:

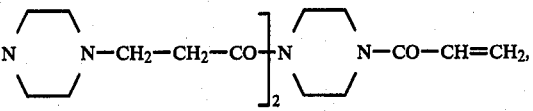

Example IVb in Ser. No. 762,804. It is obtained with the same polycondensate as in product $B_5$, but crosslinked with methylene bis-acrylamide, at a rate of 16 moles of crosslinking agent per 100 amine groups of the polycondensate;

(7) compound $B_7$ which is the compound described in Example IIIa of Ser. No. 762,804. It is obtained with the which is prepared by reacting piperazine bis-acrylamide on piperazine in molar proportions of 3:2. 10.2 moles of crosslinking agent per 100 amine groups of the polycondensate are used;

(14) compound $B_{14}$ is obtained from the same polycondensate as $B_1$, which is then crosslinked with a material of the formula

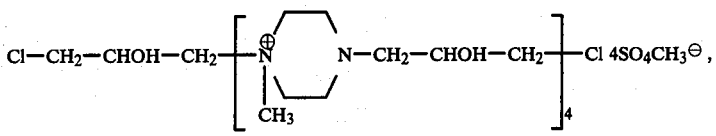

same polycondensate as $B_4$, but it is crosslinked with epichlorohydrin (7.8 moles per 100 amine groups of the polycondensate);

(8) compound $B_8$ which is the compound described in Example VIa of Ser. No. 762,804. It is obtained by the polycondensation of methyl methacrylate (2 moles) and ethylene diamine (1 mole) with diethylenetriamine (1 mole) which is then crosslinked with methylene bis-acrylamide (21.4 moles per 100 amine groups of the polycondensate);

(9) compound $B_9$ which is the compound described in Example IIa of Ser. No. 762,804. It is obtained by the polycondensation of adipic acid (3 moles) and a mixture of piperazine (1 mole) and diethylenetriamine (2 moles) which is then crosslinked with epichlorohydrin (13.2 moles per 100 amine groups of the polycondensate);

(10) compound $B_{10}$ which is obtained from the same polycondensate as $B_1$, crosslinked with N,N'-bis-acryloyl piperazine;

(11) compound $B_{11}$ is obtained from the same polycondensate as for $B_1$, crosslinked with the following material:

6.33 moles of crosslinking agent per 100 amine groups of the polycondensate are used. The crosslinking agent is obtained by quaternization with dimethyl sulfate of the crosslinking agent used for compound $B_{11}$;

(15) compound $B_{15}$ is obtained from the same polycondensate as $B_1$, which is then crosslinked with the material:

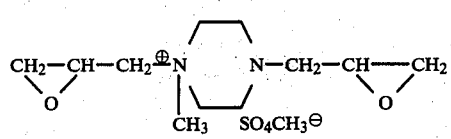

9.8 moles of crosslinking agent per 100 amine groups of the polycondensate are used;

(16) compound $B_{16}$ is obtained from the same polycondensate as $B_1$ which is then crosslinked with:

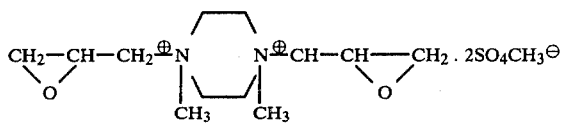

7.6 moles of crosslinking agent per 100 amine groups of the polycondensate are used;

(17) compound $B_{17}$ which is the compound described in Example Va of Ser. No. 762,804. It is obtained by the polycondensation of a mixture of 2 moles of methyl acrylate and 1 mole of ethylenediamine with 1 mole of diethylenetriamine, the said polycondensate then being crosslinked with epichlorohydrin (11 g per 200 g of the polycondensate);

(18) compound $B_{18}$ which is the compound described in Example Id of Ser. No. 762,804. It is obtained from the same polycondensate as $B_1$, which is then crosslinked with divinylsulfone, at a rate of 13.9 moles of divinylsulfone per 100 amine groups of the polycondensate;

(19) compound $B_{19}$ is an adipic acid-diethylene triamine polycondensate quaternized by bis-epoxypropyl dimethyl ammonium chloride, sold under the name CARTARETINE F. 4 and F. 8 by Sandoz;

(20) compound $B_{20}$ is obtained from the same polycondensate as $B_1$ which is then crosslinked with the material:

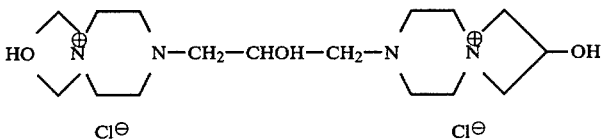

which is prepared by reacting 1,3-bis-piperazinyl-2-propanol (50 g) on epichlorohydrin (43.5 g). 8 moles of crosslinking agent per 100 moles of amine groups of the polycondensate are used;

(21) compound $B_{21}$ is obtained from the same polycondensate as $B_1$ which is then crosslinked with the reaction product of piperazine (3 moles), epichlorohydrin (4 moles) and NaOH (2 moles). 5.8 moles of crosslinking agent per 100 moles of amine groups of the polycondensate are employed;

(22) compound $B_{22}$ is obtained from the same polycondensate as $B_1$ which is then crosslinked with a crosslinking agent of a statistical composition obtained by reacting piperazine (2 moles), epichlorohydrin (3 moles) and NaOH (1 mole). 7.36 moles of crosslinking agent per 100 amine groups of the polycondensate are used; and

(23) compound $B_{23}$ is an adipic acid/epoxy propyl diethylenetriamine copolymer sold under the name Delsette 101.

The quaternized polymers of Formula I which are used in the compositions of the present invention in combination with the said crosslinked polyamino-amides are principally those for which $R_1$ and $R_2$ represent methyl, ethyl, propyl, 2-hydroxy ethyl, 2-hydroxy propyl or 3-hydroxy propyl; $R_3$ and $R_4$ represent methyl, ethyl or n-propyl; or $R_2=R_4=R_1=CH_3$ and $R_3$ represents a $C_8$-$C_{12}$ alkyl, cyclohexyl or benzyl; or $R_2=R_4=CH_3$ and $R_1=R_3$, $R_1$ and $R_3$ representing $C_2$-$C_8$ alkyl; A and B each independently represent —$CH_2$—$C_6H_4$—$CH_2$— or —$(CH_2)_y$—CH(E)—$(CH_2)_x$—CH(K)—$(CH_2)_t$— wherein x, y and t are whole numbers ranging from 0 to 11 and such that the sum (x+y+t) is greater than or equal to 0 and lower than 18, and E and K represent hydrogen or an aliphatic radical having less than 18 carbon atoms; or A and B represent 2-hydroxypropylene or divalent ethyleneoxyethylene or propyleneoxypropylene, or the groups —$(CH_2)_3$—NH—CO—NH—$(CH_2)_3$—.

The quaternized polymers useful in the compositions of the present invention are known and can be prepared for example in accordance with the procedures described in French Patent application Nos. 75.15162, 76.20261 and 74.19711.

In the compositions of the present invention, the crosslinked polyamino-amides are present in an amount of 0.1 to 5, and preferably from 0.1 to 3, weight percent, and the quaternized polymers are present in an amount of 0.1 to 10, and preferably from 0.1 to 5, weight percent, based on the total weight of the composition.

In accordance with a preferred embodiment, the compositions of the present invention also contain from 0.2 to 2 weight percent of the phosphoric ester of a fatty alcohol, optionally polyethoxylated, with for example up to 20 moles of ethylene oxide, the fatty alcohol being principally an alcohol having 12 to 18 carbon atoms, optionally unsaturated. Representative phosphoric esters include principally such commercial products as DIVALINE SO and DIVALINE SO NEU (Zshimmer and Schwarz) and HOSTAPHAT (Hoechst). These compositions impart to the hair a particular brightness and softness.

The compositions for the hair in accordance with the present invention can be provided in the form of an aqueous or hydroalcohol solution, wherein the alcohol is a lower alcohol, such as ethanol or isopropanol, or under the form of a cream, a gel, or an emulsion. In addition to the components mentioned above, the compositions include, generally, an adjuvant conventionally employed in cosmetic compositions for the hair. The adjuvants generally present in these cosmetic compositions are, for example, perfumes, dyes, preservatives, sequesterants, thickening agents, emulsifiers and the like.

The cosmetic compositions for the hair in accordance with the present invention constitute principally treating creams for application before or after a hair dyeing or hair bleaching operation, before or after a shampoo, before or after a permanent wave operation; a hair dye product; a shampoo; a rinse lotion for application before or after a shampoo, between successive shampoos, before or after a hair dyeing or hair bleaching operation, or before or after a permanent wave operation; a hair setting lotion; a brushing lotion; and a hair restructuring lotion.

(1) When the compositions of the present invention constitute treating creams, these creams are produced with a support formulated from a soap or fatty alcohol in the presence of an emulsifying agent. The soap can be constituted from natural or synthetic $C_{12}$–$C_{18}$ fatty acids (such as lauric acid, myristic acid, palmitic acid and stearic acid) at concentrations between 10 and 30% and alkalizing agents (such as NaOH, KOH, ammonia, monoethanolamine, diethanolamine and triethanolamine).

These creams can contain, in addition to the mixture of quaternary polymers and polyamino-amide and soap, such adjuvants as fatty amides and fatty alcohols.

Representative fatty amides that can be used include, in particular, the following compounds; the mono or di-ethanolamides of the acids derived from copra, of lauric acid or of oleic acid, in concentrations ranging from 0 to 10 weight percent.

Representative fatty alcohols include, in particular, oleyl alcohol, myristyl alcohol, cetyl alcohol, stearyl alcohol and isostearyl alcohol in amounts ranging between 0 and 10 weight percent.

The creams can also be formulated from $C_{12}$–$C_{18}$ natural or synthetic alcohols in admixture with emulsifiers. Representative fatty alcohols include, in particular, copra alcohol, myristyl alcohol, cetyl alcohol, stearyl alcohol and hydroxy stearyl alcohol, in amounts between 5 and 25 weight percent.

Representative emulsifiers include:

(a) fatty alcohols, oxyethylenated or polyglycerolated such as for example, oleyl alcohol polyoxyethylenated with 10–30 moles of ethylene oxide, cetyl alcohol oxyethylenated with 6–10 moles of ethylene oxide, cetyl stearyl alcohol oxyethylenated with 10 moles of ethylene oxide, oleo cetyl alcohol oxyethylenated with 30 moles of ethylene oxide, stearyl alcohol oxyethylenated with 10–15 or 20 moles of ethylene oxide, oleyl alcohol polyglycerolated with 4 moles of glycerol and $C_9$–$C_{15}$ synthetic fatty alcohols polyoxyethylenated with 5 or 10 moles of ethylene oxide. These "non-ionic" emulsifiers are present in an amount of 5 to 25 weight percent; and (b) alkyl sulfates, oxyethylenated or not, such as sodium lauryl sulfate, ammonium lauryl sulfate, sodium cetyl stearyl sulfate, triethanolamine cetyl stearyl sulfate, mono- or tri-ethanolamine lauryl sulfate, sodium lauryl ether sulfate oxyethylenated with for example 2.2 moles of ethylene oxide and monoethanolamine lauryl ether sulfate oxyethylenated with, for example, 2.2 moles of ethylene oxide. These emulsifiers are present in an amount between 3 to 15 weight percent.

These creams can also contain, in addition to the polymers, such adjuvants as fatty amides. Representative fatty amides include, for example, oleic diethanolamide, copra mono- or di-ethanolamide and stearic monoethanolamide, in an amount between 0 and 10 weight percent.

(2) When the compositions of the present invention constitute hair dye creams, they include, in addition to the quaternary polymer and the crosslinked polyamino-amide, various components which impart a cream form to the composition, these components being analogous to those defined above. There are also included in these compositions an alkalizing agent and one or more hair dyes.

The pH of these compositions is generally between 9 and 11, the pH being regulated by the addition of an appropriate alkalizing agent in the dye support. Representative alkalizing agents include ammonia, monoethanolamine, diethanolamine or triethanolamine.

The hair dyes employed belong to the class of oxidation dyes to which can be added direct dyes, such as an azo, an anthraquinone and a nitrobenzene dye, or an indamine, an indoaniline, an indophenol or other oxidation dyes such as the leucoderivatives of these compounds.

the said "oxidation dyes" are aromatic compounds of the diamine, aminophenol or phenol type. These aromatic compounds are precursors of dyes which are transformed into dye compounds by condensation in the presence of a large excess of an oxidizing agent, generally $H_2O_2$. A distinction is made between oxidation dyes, on the one hand, i.e. "bases" which are ortho or para diamines or ortho or para mono- or diaminophenols and on the other hand "modifiers" which are m-diamines, m-aminophenols or polyphenols.

The "bases" principally employed are: p-phenylene diamine, p-toluylene diamine, chloroparaphenylene diamine, p-aminodiphenylamine, o-phenylenediamine, o-toluylene diamine, 2,5-diamino anisole, o-aminophenol and p-aminophenol.

The "modifiers" principally used are: m-phenylene diamine, m-toluylene diamine, 2,4-diamino anisole, m-aminophenol, pyrocatechol, resorcinol, hydroquinone, α-naphthol, 1,5-dihydroxy naphthalene and 2,6-diaminopyridine.

The "bases" are also called basic oxidation dyes and the "modifiers" are also called "couplers".

(3) When the compositions of the present invention constitute shampoos, they contain, in addition to the quaternized polymer and the crosslinked polyamino-amide, at least one anionic, cationic, non-ionic or amphoteric detergent.

Representative anionic surfactants include, principally, the following compounds, as well as mixtures thereof:

(a) the alkali salts, the magnesium salts, the ammonium salts, the amine salts or the amino alcohol salts of the following compounds:

(i) alkyl sulfates, alkyl ether sulfates wherein the alkyl has a $C_{12}$–$C_{18}$ linear chain, alkylamide sulfates and ethoxylated ether sulfates having $C_{12}$ to $C_{18}$ linear chains and alkylaryl polyethersulfates monoglyceride sulfates, (ii) alkyl sulfonates wherein the alkyl has a $C_{12}$–$C_{18}$ linear chain, alkylamide sulfonates, alkyl aryl sulfonates, α-olefin sulfonates with $C_{12}$–$C_{18}$ linear chains.

(iii) alkylsulfosuccinates, alkylethersulfosuccinates, alkylamide sulfosuccinates wherein the alkyl has a $C_{12}$–$C_{18}$ linear chain, (iv) alkylsulfosuccinamates wherein the alkyl has a $C_{12}$–$C_{18}$ linear chain, (v) alkyl sulfoacetates wherein the alkyl has a $C_{12}$–$C_{18}$ chain, (vi) alkyl phosphates, alkyletherphosphates wherein the alkyl has a $C_{12}$–$C_{18}$ chain, and (vii) alkylsarcosinates, alkylpolypeptides, alkyl amidopolypeptidates, alkylisethionates and alkyl taurates wherein the alkyl has a $C_{12}$–$C_{18}$ chain, and (b) fatty acids such as oleic acid, ricinoleic acid, palmitic acid, stearic acid, copra oil acid or hydrogenated copra oil acid, carboxylic acids of polyglycolic ethers of the formula Alk—$(OCH_2—CH_2)_1$ —$_{OCH_2}$—$CO_2H$, wherein Alk represents a $C_{12}$–$C_{18}$ linear chain and $n_1$ a whole number varying from 5 to 15.

Representative cationic surfactants which can be used alone or in admixture include principally:

(i) salts of fatty amines such as alkylamine acetates, (ii) quaternary ammonium salts such as alkyldimethyl benzyl ammonium chloride or bromide, alkyltrimethyl ammonium chloride or bromide, alkyldimethylhydroxyethyl ammonium chloride or bromide, dimethyldistearyl ammonium chloride or bromide, and the methosulfates of alkylamido ethyltrimethyl ammonium chloride or bromide, (iii) alkyl pyridinium salts and (iv) imidazoline derivatives.

Further, compounds having a cationic character, such as amine oxides (alkyldimethylamine oxide or alkylaminoethyl dimethylamine oxide) can also be used.

Representative non-ionic surfactants which can optionally be used in admixture with the preceding anionic surfactants include:

(i) the condensation product of a mono alcohol, an α-diol, an alkylphenol or an amide with glycidol, for example, compounds of the formula $R-CHOH-CH_2-O+CH_2-CHOH-CH_2-O)_{n_2}H$ wherein R represents an aliphatic, cycloaliphatic or arylaliphatic radical having 7–12 carbon atoms and mixtures thereof, the aliphatic chains being able to carry ether, thioether and hydroxy methylene groups and $n_2$ being a whole number such that $1 \leq n_2 \leq 10$ and compounds of the formula $RO+C_2H_3O(CH_2OH)+_{n_3}H$ wherein R represents alkyl, alkenyl or alkylaryl, having 8–22 carbon atoms and $1 \leq n_3 \leq 10$, (ii) alcohols, alkylphenols or fatty acids polyethoxylated or polyglycerolated having $C_8-C_{18}$ linear fatty chains carrying most often from 2 to 15 moles of ethylene oxide, (iii) copolymers of ethylene oxide and propylene, (iv) condensates of ethylene oxide and propylene on fatty alcohols, (v) polyethoxylated fatty amides, (vi) polyethoxylated fatty amines, (vii) ethanolamides, (viii) fatty acid esters of glycol, (ix) fatty acid esters of sorbitol and (x) fatty acid esters of sucrose.

Representative amphoteric surfactants which can be used include principally:

(i) alkylamino mono- and di-propionates, (ii) betaines, such as N-alkyl betaines, N-alkylsulfobetaines and N-alkylamido betaines, and (iii) cycloimidiniums (alkylimidazolines).

All these detergents, as well as numerous others not mentioned here but equally useful in the shampoo compositions of the present invention, are well known and are described in the literature.

The compositions in the form of shampoos can also contain various adjuvants such as for example, perfumes, dyes, preservatives, thickening agents, foam stabilizers, softening agents or one or more cosmetic resins.

In these shampoo compositions the detergent concentration is generally between 3 and 50 weight percent, relative to the total weight of the composition, and preferably from 3 to 20 weight percent. The pH is generally between 3 and 9.

(4) When the compositions of this invention constitute lotions, they can be hair styling lotions, forming lotions (called brushing lotions), non-rinse hair reinforcing lotions, rinse lotions (called rinses) and restructuring lotions.

The rinse lotions have been defined above.

By forming lotions or brushing lotions is meant a lotion which is applied after a shampoo and which favors forming or shaping the hair, this forming being effected on wet hair with the aid of a brush, while drying the hair with a hand dryer.

By non-rinse hair set reinforcing lotions is meant a lotion which is applied after a shampoo and before a hair set. This lotion, which is not rinsed off, facilitates the ultimate hair set and improves its durability.

These lotions include, in a aqueous, alcoholic or hydroalcoholic solution, at least one quaternized polymer and at least one crosslinked polyamino-amide such as defined above. They can also contain:

(a) film-forming polymers such as polyvinylpyrrolidone, copolymers of vinylpyrrolidone and vinyl acetate and copolymers of vinyl acetate and a vinyl alkyl ether.

Representative preferred resins include polyvinylpyrrolidone having a molecular weight from 10,000 to 70,000; copolymers of vinylpyrrolidone (VP) and vinyl acetate (VA) having a molecular weight from 30,000 to 200,000, the ratio VP:VA being between 30:70 and 70:30; and methyl methacrylate (15–25%)/stearyl methacrylate (18–28%)/dimethylaminoethyl methacrylate (52–62%) terpolymers quaternized or not by dimethyl sulfate;

(b) quaternary vinylpyrrolidone copolymers such as for example, a polymer having a molecular weight in the order of 1,000,000 and sold under the name GAFQUAT 755 by GAF and a polymer having a molecular weight in the order of 100,000 and sold under the name GAFQUAT 734 by GAF, graft cationic copolymers resulting from the copolymerization of 3–95 weight percent N-vinylpyrrolidone, 3–95 weight percent dimethylaminoethyl methacrylate and 2–50 weight percent of polyethylene glycol, such as those described in French Pat. No. 76.15948, cationic polymers resulting from the condensation of piperazine or its derivatives (1) or bifunctional compounds such as alkyl or alkylaryl dihalides, bis-epoxides, epihalohydrins, bis unsaturated derivatives and/or (2) on a primary amine both hydrogen atoms of which can be substituted and which acts as a bifunctional compound; (3) both on an epihalohydrin and on a hydroxylated amine such as diglycolamine, 2-amino-2-methyl 1,3-propanediol or on an amino acid such as glycocoll, and a quaternized cellulose such as JR 400, sold by Union Carbide.

In these lotions, the amount of the adjuvant polymer is generally between 0.1 and 5, preferably between 0.1 and 3, weight percent. The pH is generally between 3 and 9.

By rinse lotion is meant a lotion that is applied before or after a shampoo, or between successive shampoos, or before or after hair dyeing or hair bleaching, before or after a permanent wave. These rinse lotions provide a hair conditioning effect and are rinsed off the hair after an appropriate contact time therewith.

These rinse lotion compositions can be an aqueous or hydroalcoholic solution including or not surfactants; an emulsion; or gels. Further, these compositions can be pressurized in an aerosol container together with an appropriate aerosol propellant.

Representative surfactants usefully employed are principally non-ionic or cationic surfactants such as those set forth above in the description of the shampoo compositions of this invention, and more particularly:

(i) condensation products of a mono alcohol, an α-diol, and alkyl phenol or an amide with glycidol, for example, compounds of the formula $R-CHOH-CH_2-O-(CH_2-CHOH-CH_2-O)_{n_2}H$ wherein R represents an aliphatic, cycloaliphatic or aryl aliphatic radical having from 7-21 carbon atoms and mixtures thereof, the aliphatic chains being able to carry ether, thioether and hydroxymethlene and $1 \leq n_2 \leq 10$; and compounds of the formula $RO + C_2H_3O(CH_2OH) +_{n_3} H$, wherein R represents alkyl, alkenyl or alkylaryl, containing 8-22 carbon atoms, and $1 \leq n_3 \leq 10$; and (ii) alcohols, alkylphenols or fatty acids, polyethoxylated or polyglycerolated, having a linear fatty chain of $C_8$-$C_{18}$, carrying most often 2-15 moles of ethylene oxide.

The surfactant concentration can vary from 0 to 7 weight percent.

An anionic or amphoteric surfactant can also be employed.

When the compositions of the present invention are provided in the form of emulsions, they can be non-ionic or anionic emulsions. The non-ionic emulsion is a mixture of oils, and/or waxes, fatty alcohols and polyethoxylated fatty alcohols, such as polyethoxylated stearyl or cetyl stearyl alcohol. Cations can be added to these compositions.

The anionic emulsions are constituted from soaps. Representative anionic emulsions include the emulsion sold under the name Imwitor 960 K by Dynamit Nobel, and the emulsions sold under the names Lameform ZEM, LPM and NSM by Grunau.

When the compositions are provided in the form of a gel, they contain thickening agents in the presence or not of solvents.

The thickening agent can be sodium algenate or gum arabic or cellulose derivatives such as methyl cellulose, hydroxy methyl cellulose, hydroxy ethyl cellulose or hydroxypropyl cellulose. The thickening of the lotion can also be effected by a mixture of polyethylene glycols and polyethylene glycol stearates or distearates, or by a mixture of phosphoric esters and amides.

The thickening agent concentration can vary from 0.5 to 30, and preferably from 0.5 to 15, percent by weight The pH of the rinse lotions ranges generally from 2 to 9.5.

When the compositions of the present invention constitute restructuring lotions, they contain products for reinforcing the keratin chain of the hair, such as methylol derivatives including those described in French Pat. Nos. 1,527,085 and 1,579,979.

As has been indicated above, the compositions according to the present invention prevent the appearance of a harsh feel of the hair which is generally observed during repeated application of known conditioning lotions containing only the crosslinked polyamino-amides such as defined above. After several shampoos, the lessening of this effect of a harsh feel is not observed when the crosslinked polyamino-amide is combined with cationic agents other than that defined and employed herein and, in particular, other cationic polymers such as the GAFQUATS, defined above.

Further, it has been observed that the application to the hair of compositions such as defined in the present invention also protects the hair against the effects of subsequently employed hair degrading cosmetic treatments, such as hair dyeing, hair bleaching and permanent waving operations. It has been discovered that the combination of the crosslinked polyamino-amides with the particular class of quaternized polymers defined above provides a hair protective effect. Such an effect has not been observed when these crosslinked polyamino-amides are combined with other cationic agents.

Additionally the application to the hair of the compositions according to the present invention does not produce any harmful or undesired effect such as a greasy appearance or feel of the hair.

The present invention also relates to a process for conditioning the hair, comprising applying to the hair an effective amount of the composition defined above so as to obtain the desired conditioning effect.

The following non-limiting examples are given to illustrate the present invention.

Although the compounds designated by the letters A and B with appropriate numerical subscripts are generally introduced during the preparation of a given composition, in the form of a solution, in the Examples detailing the formulation, only the weight of the active material (i.e. A and B) has been given.

Further, in these examples, the perfume, when it is present, represents from 0.1 to 0.2 weight percent of the compositions and the dyes, when present, in compositions other than hair dyes, is present in amounts of 0.01 to 0.15 weight percent relative to the weight of the composition. Also an alcoholic solution of "n" degrees contains n % alcohol by volume.

Unless otherwise stated, all parts and percentages are by weight.

EXAMPLE 1—Treating Cream

1a—A cream having the following composition is prepared:

| | |
|---|---|
| Cetyl stearyl alcohol | 15 g |
| Oleic diethanolamide | 3 g |
| Sodium cetyl stearyl sulfate | 3 g |
| Compound $A_1$ | 1.0 g |
| Compound $B_1$ | 0.5 g |
| Phosphoric acid ester of ethoxylated oleyl alcohol, sold under the name Divaline SO | 1.0 g |
| Water, sufficient for | 100 g |

10-15 g of this cream are applied to natural hair, moist and dried, taking care to thoroughly impregnate the hair. The cream is permitted to remain in contact with the hair for 10 minutes, after which it is rinsed off. The wet hair, thus treated, untangles easily and is soft to the touch.

The hair is then set and dried under a hood. The dry hair untangles easily and is silky to the touch. The hair is shiny and lively; it has body and is full.

Compound $A_1$ is a compound of Formula I wherein $A=(CH_2)_3$; $B=(CH_2)_6$; $R_1=R_2=R_3=R_4=CH_3$; and $X^\ominus = Cl^\ominus$.

Similar results are achieved using creams having the following compositions:

1b

| | |
|---|---|
| Cetyl stearyl alcohol | 20 g |
| Oleic diethanolamide | 2 g |
| Sodium cetyl stearyl sulfate | 2 g |
| Compound $A_2$ | 1.3 g |
| Compound $B_2$ | 1 g |
| Divaline SO | 0.8 g |
| Dyes, Perfume | |
| Water, sufficient for | 100 g |

Compound $A_2$ is a compound of Formula I wherein $A=(CH_2)_6$; $B=(CH_2)_4$; $R_1=R_2=R_3=R_4=CH_3$; and $X^\ominus = Br^\ominus$.

1c

| | | |
|---|---|---|
| Cetyl alcohol | 15 g | |
| Coco monoethanolamide | 4 g | |
| Ammonium lauryl sulfate | 3 g | |
| Compound $A_3$ | 1.2 g | |
| Compound $B_2$ | 0.4 g | |
| Dyes, Perfume | | |
| Water, sufficient for | 100 g | |

Compound $A_3$ is a compound of Formula I wherein $A=(CH_2)_6$; $B=(CH_2)_8$; $R_1=R_2=R_3=R_4=CH_3$; and $X^\ominus = Br^\ominus$.

1d

| | |
|---|---|
| Cetyl alcohol | 15 g |
| Coco monoethanolamide | 4 g |
| Ammonium lauryl sulfate | 3 g |
| Compound $A_3'$ | 1.2 g |
| Compound $B_{19}$ | 0.4 g |
| Dyes, Perfume | |
| Water, sufficient for | 100 g |

Compound $A_3'$ is a compound of Formula I wherein $A=(CH_2)_3-NH-CO-NH-(CH_2)_3$; $B=-(CH_2)_2-O-(CH_2)_2$; $R_1=R_2=R_3=R_4=CH_3$; and $X^\ominus=Cl^\ominus$.

1e

| | |
|---|---|
| Cetyl stearyl alcohol | 20 g |
| Oleic diethanolamide | 2 g |
| Sodium cetyl stearyl sulfate | 2 g |
| Compound $A_2$ | 1.3 g |
| Compound $B_{19}$ | 0.5 g |
| Phosphoric acid ester of ethoxylated oleyl alcohol, sold under the name Divaline SO | 0.8 g |
| Dyes, Perfume | |
| Water, sufficient for | 100 g |

EXAMPLE 2—Treating Creams For Use After Oxidation Dyeing of the Hair

2a—A cream having the following composition is prepared:

| | |
|---|---|
| Cetyl stearyl alcohol | 16 g |
| Oleic diethanolamide | 5 g |
| Sodium cetyl stearyl alcohol | 3 g |
| Compound $A_1$ | 1.5 g |
| Compound $B_1$ | 1.0 g |
| Divaline SO | 1.6 g |
| Water, sufficient for | 100 g |

10–15 g of this cream are applied to wet hair after having rinsed therefrom the material employed in the oxidation dyeing of the hair. The cream is permitted to remain in contact with the hair for 2–3 minutes at which time it is then rinsed off. The wet hair combs easily and is soft to the touch. The hair is then set and dried under a hood. The dry hair combs easily; has a silky touch; is shiny and lively; and has body and fullness.

The compound $A_1$ is defined above.

Similar results are achieved using creams having the following compositions:

2b

| | |
|---|---|
| Cetyl stearyl alcohol | 20 g |
| Coco monoethanolamide | 4 g |
| Sodium cetyl stearyl sulfate | 4 g |
| Compound $A_4$ | 2.5 g |
| Compound $B_3$ | 1 g |
| Water, sufficient for | 100 g |

Compound $A_4$ is a compound of Formula I wherein $A=(CH_2)_3$; $B=(CH_2)_4$; $R_1=R_2=R_3=R_4=CH_3$; and $X^\ominus=Br^\ominus$.

2c

| | |
|---|---|
| Cetyl alcohol | 25 g |
| Oleyl diethanolamide | 2 g |
| Ammonium lauryl sulfate | 3 g |
| Compound $A_5$ | 1.5 g |
| Compound $A_4$ | 0.8 g |
| Divaline SO | 1 g |
| Water, sufficient for | 100 g |

Compound $A_5$ is a compound of Formula I wherein $A=(CH_2)_6$; $B=(CH_2)_2-O-(CH_2)_2-$; $R_1=R_2=R_3=R_4=CH_3$; and $X^\ominus=Br^\ominus$.

2d

| | |
|---|---|
| Myristyl alcohol | 18 g |
| Coco monoethanolamide | 8 g |
| Sodium cetyl stearyl sulfate | 3 g |
| Compound $A_6$ | 1.2 g |
| Compound $B_5$ | 1 g |
| Water, sufficient for | 100 g |

Compound $A_6$ is a compound of Formula I wherein $A=(CH_2)_2$ $B=(CH_2)_6$; $R_1=R_2=R_3=R_4=CH_3$; and $X^\ominus=Br^\ominus$.

2e

| | |
|---|---|
| Cetyl stearyl alcohol | 15 g |
| Oleic diethanolamide | 8 g |
| Ammonium lauryl sulfate | 3 g |
| Compound $A_7$ | 1.4 g |
| Compound $B_6$ | 1.1 g |
| Divaline SO | 0.7 g |
| Water, sufficient for | 100 g |

Compound $A_7$ is a compound of Formula I wherein $A=(CH_2)_3$; $B=(CH_2)_6$; $R_1=R_2=R_3=R_4=CH_3$; and $X^\ominus=Br^\ominus$.

2f

| | |
|---|---|
| Cetyl alcohol | 17 g |
| Coco monoethanolamide | 5 g |
| Sodium cetyl stearyl sulfate | 3 g |
| Compound $A_7$ | 0.7 g |
| Compound $A_8$ | 0.5 g |
| Compound $B_7$ | 0.9 g |
| Water, sufficient for | 100 g |

Compound $A_8$ is a compound of Formula I wherein $A=(CH_2)_6$; $B=CH_2-CHOH-CH_2$; $R_1=R_2=R_3-R_4=CH_3$; and $X^\ominus=Br^\ominus$. Compound $A_7$ has the meaning given above.

2g

| | |
|---|---|
| Cetyl stearyl alcohol | 7 g |
| Oleocetyl alcohol oxyethylenated with 30 moles of ethylene | |

| | |
|---|---|
| oxide, sold under the name Mirystill OC 30 | 1.5 g |
| Oleic acid | 1.3 g |
| Compound $A_9$ | 1.5 g |
| Compound $B_8$ | 1 g |
| Monoethanolamine | 0.4 g |
| Water, sufficient for pH, adjusted to 8 | 100 g |

Compound $A_9$ is a compound of Formula I wherein $A=(CH_2)_6$; $B=(CH_2)_5$; $R_1=R_2=R_3=R_4=CH_3$; and $X^\ominus=Br^\ominus$.

2h

| | |
|---|---|
| Myristyl alcohol | 18 g |
| Coco monoethanolamide | 8 g |
| Sodium cetyl stearyl sulfate | 3 g |
| Compound $A_6$ | 1.2 g |
| Compound $B_{19}$ | 1 g |
| Water, sufficient for | 100 g |

EXAMPLE 3—Care Creams

3a—A cream having the following composition is prepared:

| | |
|---|---|
| Stearyl alcohol | 20 g |
| Stearyl alcohol oxyethylenated with 10 moles of ethylene oxide, sold under the name BRIJ 76 | 8 g |
| Compound $A_1$ | 2 g |
| Compound $B_1$ | 1 g |
| Divaline SO | 1.5 g |
| Water, sufficient for | 100 g |

This cream is applied to natural hair, wet and dry, in an amount sufficient (80–100g) to thoroughly impregnate and cover the hair. The cream is permitted to remain in contact with the hair for 30–45 minutes at which time it is then rinsed off. The wet hair is very soft and easy to comb. The hair is then set and dried under a hood. The dry hair combs easily; has a silky touch; is shiny and lively; and has body or fullness. This effect lasts after several shampooings.

Essentially similar results are achieved using the following creams in the same manner indicated above.

3b

| | |
|---|---|
| Cetyl alcohol | 22 g |
| Cetyl alcohol oxyethylenated with 10 moles of ethylene oxide, sold under the name BRIJ 56 | 10 g |
| Compound $A_1$ | 1.2 g |
| Compound $B_{11}$ | 0.5 g |
| Divaline SO | 1.2 g |
| Water, sufficient for | 100 g |

3c

| | |
|---|---|
| Stearic acid | 10 g |
| Cetyl stearyl alcohol oxyethylenated with 10 moles of ethylene oxide | 3 g |
| Monoethanolamine | 0.5 g |
| Glycerine | 2 g |
| Compound $A_4$ | 3 g |
| Compound $B_1$ | 1.5 g |
| Perfume - Dyes Water, sufficient for pH is adjusted to 7. | 100 g |

50–80 grams of this cream are applied to dirty, wet hair and the hair is thoroughly impregnated with the cream by rubbing. The cream is permitted to remain in contact with the hair for 30–45 minutes. Thereafter the hair is shampooed. The wet hair is very soft and easy to comb. After setting and drying the hair, it has a particularly soft touch or feel. The hair thus treated is shiny, lively and has body. This effect lasts after several shampooings.

Essentially similar results are achieved using the following cream composition by applying the cream before a shampooing operation.

3d

| | |
|---|---|
| Palmitic acid | 12 g |
| Monoethanolamine | 0.6 g |
| Glycerine | 3 g |
| Compound $A_{10}$ | 3 g |
| Compound $A_{11}$ | 4 g |
| Compound $B_9$ | 2 g |
| Perfume, Dyes Water, sufficient for pH, adjusted to 6 | 100 g |

Compound $A_{10}$ is a compound of Formula I wherein $A=(CH_2)_2$; $B=(CH_2)_4$; $R_1=R_2=R_3=CH_3$; $X^\ominus=Br^\ominus$.

Compound $A_{11}$ is a compound of Formula I wherein $A=(CH_2)_3$; $B=CH_2-CHOH-CH_2-$; $R_1=R_2=R_3=R_4=CH_3$; $X^{63}=Br^\ominus$.

3e

| | |
|---|---|
| Cetyl alcohol | 20 g |
| Cetyl alcohol oxyethylenated with 10 moles of ethylene oxide, sold under the name BRIJ | 12 g |
| Compound $A_1$ | 1.5 g |
| Compound $B_{10}$ | 0.5 g |
| Divaline SO | 1 g |
| Water, sufficient for | 100 g |

3f

| | |
|---|---|
| Stearyl alcohol | 15 g |
| Cetyl stearyl alcohol oxyethylenated with 10 moles of ethylene oxide | 8 g |
| Monoethanolamine | 2 g |
| Glycerine | 5 g |
| Compound $A_1$ | 1 g |
| Compound $B_{12}$ | 0.5 g |
| Perfumes, Dyes Water, sufficient for pH, adjusted to 7 | 100.0 g |

3g

| | |
|---|---|
| Stearic acid | 10 g |
| Cetyl stearyl alcohol oxyethylenated with 10 moles of ethylene oxide | 3 g |
| Monoethanolamine | 0.5 g |
| Glycerine | 2 g |
| Compound $A_3'$ | 3 g |

-continued

| | |
|---|---|
| Compound $B_{19}$ | 1.5 g |
| Perfumes, Dyes | |
| Water, sufficient for | 100 g |
| pH, adjusted to 7 | |

Essentially similar results are achieved by applying the following creams to the hair before shampooing the hair.

3h

| | |
|---|---|
| Stearic acid | 12 g |
| Cetyl stearyl alcohol oxyethylenated with 10 moles of ethylene oxide | 4 g |
| Monoethanolamine | 2 g |
| Glycerine | 4 g |
| Compound $A_1$ | 1.2 g |
| Compound $B_{14}$ | 0.5 g |
| Perfumes, Dyes | |
| Water, sufficient for | 100 g |
| pH, adjusted to 7 | |

3i

| | |
|---|---|
| Stearic acid | 10 g |
| Cetyl stearyl alcohol oxyethylenated with 10 moles of ethylene oxide | 6 g |
| Monoethanolamine | 2 g |
| Glycerine | 4 g |
| Compound $A_1$ | 1 g |
| Compound $B_{15}$ | 0.6 g |
| Perfumes, Dyes | |
| pH, adjusted to 7 | |

3j

| | |
|---|---|
| Stearic acid | 15 g |
| Cetyl stearyl alcohol oxyethylenated with 10 moles of ethylene oxide | 7 g |
| Monoethanolamine | 3 g |
| Glycerine | 5 g |
| Compound $A_1$ | 1 g |
| Compound $B_{16}$ | 0.6 g |
| Perfumes, Dyes | |
| Water, sufficient for | 100 g |
| pH, adjusted to 7 | |

EXAMPLE 4—Hair Restructing Lotions

4a—There is mixed, before use:
0.4 g of N,N'-di-(hydroxymethyl)ethylene thiourea with 25 ml of a solution containing:

| | |
|---|---|
| Compound $A_1$ | 0.5 g |
| Compound $B_1$ | 0.5 g |
| HCl, sufficient for | pH - 2.7 |
| Water, sufficient for | 100 ml |

This mixture is applied to washed and dried hair before setting it. The hair combs easily and is silky to the touch. The hair is then set and dried. The hair thus treated is shiny and lively; has body and fullness; is silky to the touch; and combs easily.

Essentially similar results are achieved using the following lotions:

4b

There is mixed, at the moment of use:
0.5 g of N,N-di-(hydroxymethyl)ethylene thiourea with 25 ml of a solution containing:

| | |
|---|---|
| Compound $A_{12}$ | 0.4 g |
| Compound $B_{17}$ | 0.6 g |
| HCl, sufficient for | pH - 2.5 |
| Perfumes, Dyes | |
| Water, sufficient for | 100 cc |

Compound $A_{12}$ is a compound of Formula I wherein $A=(CH_2)_6$; $B=CH_2-C_6H_4-CH_2$; $R_1=R_2=R_3=R_4=CH_3$; and $X^\ominus=Br^\ominus$.

4c

There is mixed, at the moment of use:
0.35 g of 2,4,6-tris-(hydroxymethylamino) s-triazine with 25 ml of a solution containing:

| | |
|---|---|
| Compound $A_{13}$ | 0.4 g |
| Compound $B_{18}$ | 0.6 g |
| Quaternary vinylpyrrolidone copolymer, MW = 1,000,000, sold under the mark GAFQUAT 775 | 0.2 g |
| HCl, sufficient for | pH - 2.5 |
| Perfumes, Dyes | |
| Water, sufficient for | 100 cc |

Compound $A_{13}$ is a compound of Formula I wherein $A=(CH_2)_3$; $B=(CH_2)_6$; $R_1=R_2=CH_3$; $R_3=R_4=CH_2CH_2OH$; and $X^\ominus=Br^\ominus$.

EXAMPLE 5—Rinses

5a—The following composition is prepared:

| | |
|---|---|
| Compound $B_5$ | 0.5 g |
| Compound $A_8$ | 0.5 g |
| $R-CHOH-CH_2-O-(CH_2-CHOH-CH_2-O)_{\overline{n_2}}H$ wherein R = $C_9-C_{12}$ alkyl and $n_2$ = 3.5 | 0.7 g |
| Divaline SO | 0.4 g |
| Water, sufficient for | 100 cc |
| pH = 7-8 | |

This rinse is applied to previously washed hair. The hair thus treated is easy to comb. Dry hair thus treated is particularly full, shiny and easy to style.

5b—The following composition is prepared:

| | |
|---|---|
| Compound $B_3$ | 2 g |
| Compound $A_7$ | 1 g |
| Perfumes, Dyes | |
| Water, sufficient for | 100 g |

This rinse is applied to dyes and washed hair. The hair thus treated is easy to comb. Dry hair thus treated is particularly full and easy to style. The ease of combing lasts after several shampooings.

5c—The following rinse lotion is prepared:

| | |
|---|---|
| $R-CHOH-CH_2-O-(CH_2-CHOH-CH_2-O)_{\overline{n_2}}H$ wherein R = $C_9-C_{12}$ alkyl and $n_2$ = 3.5 | 0.5 g |
| Compound $A_1$ | 0.3 g |
| Compound $B_1$ | 0.7 g |
| Water, sufficient for | 100 g |
| pH = 8.6 | |

This rinse lotion is applied to the hair before shampooing the same. It is permitted to remain in contact with the hair for a few minutes. Thereafter, it is rinsed off. Combing of the hair is facilitated and the hair has an agreeable touch or feel. The hair is both firm and soft and the liveliness of the hair style is improved.

5d—An emulsion having the following composition is prepared:

| | |
|---|---|
| Petrolatum oil | 15 g |
| Lanette wax | 2.5 g |
| Cetyl stearyl alcohol polyethoxylated with 10 moles of ethylene oxide, sold under the name SIMULSOL 1951 RD | 2.5 g |
| Compound $A_1$ | 1 g |
| Compound $B_1$ | 0.4 g |
| Water, sufficient for pH = 7.5 | 100 g |

This composition is applied to the hair before shampooing it. After application of the composition, it is rinsed off. This emulsion facilitates combing the hair and it imparts softness to the hair and provides good liveliness to the hair style.

5e—A rinse having the following composition is prepared:

| | |
|---|---|
| Compound $B_1$ | 1.2 g |
| Compound $A_1$ | 0.8 g |
| Primary amine acetate, sold under the name CATISOL AS/100 | 0.5 g |
| Water, sufficient for pH = 7.8 | 100 g |

This rinse is applied to the hair before shampooing it. It is permitted to remain in contact with the hair for a few minutes, after which it is rinsed off.

The combing of the hair is facilitated and the hair has a much more firm touch. The liveliness of the hair style is improved.

5f—The following composition is prepared:

| | |
|---|---|
| Compound $B_{19}$ | 0.5 g |
| Compound $A'_3$ | 0.5 g |
| R—CHOH—CH$_2$—O—(CH$_2$—CHOH—CH$_2$—O$\overline{)_{n_2}}$H wherein R = $C_9$-$C_{12}$ alkyl and $n_2$ = 3.5 | 0.7 g |
| Phosphoric acid ester of ethoxylated oleyl alcohol, sold under the name Divaline SO | 0.4 g |
| Water, sufficient for pH = 7-8 | 100 cc |

This rinse is applied to previously washed hair. The combing of the hair thus treated is easy. Dry hair thus treated is particularly full, shiny and easy to style.

5g—An emulsion having the following composition is prepared:

| | |
|---|---|
| Petrolatum oil | 15 g |
| Lanette wax | 2.5 g |
| Cetyl stearyl alcohol polyethoxylated with 10 moles of ethylene oxide, sold under the name SIMULSOL 1951 RD | 2.5 g |
| Compound $A_1$ | 1 g |
| Compound $B_{23}$ | 0.4 g |
| Water, sufficient for pH = 7.5 | 100 g |

This emulsion is applied to the hair before shampooing it. Thereafter, the hair is rinsed and this emulsion facilitates combing the hair and it imparts softness to the hair. The emulsion also provides good liveliness to the hair style.

EXAMPLE 6—Brushing Lotions

6a—The following composition is prepared:

| | |
|---|---|
| Compound $A_8$ | 0.35 g |
| Compound $B_1$ | 0.35 g |
| Quaternary vinylpyrrolidone copolymer, M.W. = about 100,000, sold under the name GAFQUAT 734 | 0.5 g |
| Ethyl alcohol, sufficient for 50° | |
| Perfume | |
| Water, sufficient for pH = 8.4 | 100 cc |

When applied to fine and light hair, this lotion facilitates combing the hair when wet.

When the hair is styled using the brushing technique, this lotion improves the passage of the brush therethrough and it leaves the hair soft and silky with good holding power.

6b—The following composition is prepared:

| | |
|---|---|
| Compound $A_2$ | 0.9 g |
| Compound $B_8$ | 0.3 g |
| Trimethyl cetyl ammonium bromide | 0.2 g |
| Perfume | |
| Water, sufficient for pH, adjusted to 5 | 100 cc |

When applied to dyed hair which is fine and light, this lotion facilitates combing of the hair when wet.

When the hair is styled using the brushing technique, this lotion improves the passage of the brush therethrough and it leaves the hair very soft, shiny and supple, with good holding power.

6c—The following composition is prepared:

| | |
|---|---|
| Compound $A'_3$ | 0.35 g |
| Compound $B_{23}$ | 0.35 g |
| Quaternary vinylpyrrolidone copolymer, M.W. = about 100,000, sold under the name GAFQUAT 734 | 0.5 g |
| Ethyl alcohol, sufficient for 50° | |
| Perfume | |
| Water, sufficient for pH = 8.4 | 100 cc |

EXAMPLE 7—Hair Setting Lotion

7a—The following composition is prepared:

| | |
|---|---|
| Compound $B_1$ | 0.3 g |
| Compound $A_7$ | 0.6 g |
| Ethyl alcohol, sufficient for 10° | |
| Lactic acid, sufficient for pH = 6 | |
| Perfume | |

20 cc of this lotion when applied to dyed hair provides excellent combing of the wet hair. Dry hair thus treated is shiny, soft and easy to style. This softness effect lasts several anionic shampooings.

7b—The following composition is prepared:

| | |
|---|---|
| Compound $A_2$ | 0.5 g |
| Compound $B_{17}$ | 0.5 g |
| Quaternized cellulose sold under the name JR 400 | 0.2 g |
| Ethyl alcohol, sufficient for 20° | |
| Perfumes, Dyes | |
| Water, sufficient for | 100 cc |
| pH, adjusted to 7 | |

When applied to dyed hair, this lotion facilitates untangling the hair. The dry hair is shiny and easy to style. A softness effect is achieved and it lasts after several shampooings.

7c—The following composition is prepared:

| | |
|---|---|
| Compound $B_5$ | 0.3 g |
| Compound $A_9$ | 0.3 g |
| Quaternary vinylpyrrolidone copolymer, M.W. = about 100,000 sold under the name GAFQUAT 734 | 0.5 g |
| Quaternized cellulose, sold under the name JR 400 | 0.3 g |
| Ethyl alcohol, sufficient for | 15° |
| Perfume | |
| Water, sufficient for | 100 cc |
| pH, adjusted to 8 | |

When applied to washed hair, this lotion facilitates the combing thereof. After drying and setting the hair, the hair is soft and shiny and is easy to style. This effect lasts after several shampooings.

7d—The following composition is prepared:

| | |
|---|---|
| Compound $B_3$ | 0.7 g |
| Compound $A_4$ | 0.6 g |
| Ethyl alcohol, sufficient for | 40° |
| Perfumes, Dyes | |
| Water, sufficient for | 100 cc |
| pH, adjusted to 6 | |

When applied to hair in the manner outlined in Example 7c, essentially the same favorable results are achieved.

7e—The following lotion is prepared:

| | |
|---|---|
| Compound $B_1$ | 0.2 g |
| Compound $A_5$ | 0.8 g |
| Ethyl alcohol, sufficient for 30° | |
| Perfumes, Dyes | |
| Water, sufficient for | 100 cc |
| pH, adjusted to 5 | |

When applied to hair in the manner outlined in Example 7c, essentially the same favorable results are achieved.

7f—The following composition is prepared:

| | |
|---|---|
| Quaternary vinylpyrrolidone copolymer, M. W. = about 100,000, sold under the name GAFQUAT 734 | 0.6 g |
| Quaternized cellulose, sold under the name JR 400 | 0.4 g |
| Compound $B_{17}$ | 0.35 g |
| Compound $A_2$ | 0.4 g |
| Ethyl alcohol, sufficient for 15° | |
| Lactic acid, sufficient for pH = 6.5 | |
| Water, sufficient for | 100 cc |

20 cc of this lotion when applied to natural hair facilitates the combing of the wet hair. Dry hair thus treated is particularly soft and shiny and has fullness. This softness effect lasts after several anionic shampooings.

7g—The following composition is prepared:

| | |
|---|---|
| Compound $A_8$ | 0.5 g |
| Compound $B_1$ | 0.5 g |
| Quaternary vinylpyrrolidone copolymer, M.W. = about 100,000, sold under the name GAFQUAT 734 | 0.4 g |
| Perfume, Dyes | |
| Water, sufficient for | 100 cc |

When applied to dyed hair, this lotion facilitates untangling of the wet hair. The hair thus treated when dry is soft and easy to style. This softness effect lasts after several shampooings.

7h—The following composition is prepared:

| | |
|---|---|
| Compound $B_1$ | 0.3 g |
| Compound $A'_3$ | 0.6 g |
| Ethyl alcohol, sufficient for 10° | |
| Lactic acid, sufficient for pH = 6 | |
| Perfume | |
| Water, sufficient for | 100 cc |

20 cc of this lotion when applied to dyed hair, provides excellent untangling of the hair when wet. Dry hair thus treated is shiny, soft and easy to style. This softness effect lasts after several anionic shampooings.

EXAMPLE 8—Dye Vehicles (For oxidation dyeing)

8a—A cream of the following formula is prepared:

| | |
|---|---|
| Cetyl stearyl alcohol | 16 g |
| Oleic diethanolamide | 3 g |
| Sodium cetyl stearyl sulfate | 5 g |
| Compound $B_{17}$ | 2.5 g |
| Compound $A_{14}$ | 4.5 g |
| Ammonia, 22°Bé | 10 ml |
| Paratoluylene diamine | 0.28 g |
| Para amino phenol | 0.090 g |
| Meta diamino anisole sulfate | 0.05 g |
| Resorcinol | 0.250 g |
| Meta amino phenol base | 0.070 g |
| Ethylene diamine tetraacetic acid | 1 g |
| Sodium bisulfite, d = 1.32 | 1.2 g |
| Water, sufficient for | 100 g |

30 g of this cream are admixed with 45 g of $H_2O_2$ (20 volumes) thereby providing a smooth cream which adheres well to the hair. This cream is permitted to remain in contact with the hair for 30–45 minutes, at which time the hair is then rinsed and dried. On chestnut colored hair there is obtained a light ash chestnut shade. The combing of the hair, wet or dry, is very easy.

The hair thus treated is shiny, controlled and easy to set. The hair also has body which lasts after several shampooings.

Compound $A_{14}$ is a compound of Formula I wherein $A=(CH_2)_3$; $B=(CH_2)_2-O-(CH_2)_2$; $R_1=R_2=R_3=R_4=CH_3$; and $X^\ominus=Br^\ominus$.

8b—A cream having the following formulation is prepared:

| | |
|---|---|
| Cetyl stearyl alcohol | 20 g |
| Oleic diethanolamide | 4 g |
| Sodium cetyl stearyl sulfate | 3 g |
| Compound $B_5$ | 3 g |
| Compound $A_1$ | 5 g |
| Ammonia - 22°Bé | 10 ml |
| Paratoluylene diamine | 0.2 g |
| Para amino phenol | 0.3 g |
| Resorcinol | 0.075 g |
| Meta amino phenol base | 0.070 g |
| Nitro para phenylene diamine | 0.040 g |
| Ethylene diamine tetraacetic acid | 1 g |
| Sodium bisulfite, d = 1.32 | 1 g |
| Water, sufficient for | 100 g |

30 g of this cream are mixed with 45 g of $H_2O_2$ (20 volumes), thereby providing a smooth cream which adheres well to the hair. This cream is permitted to remain in contact with the hair for 30-45 minutes, at which time the hair is then rinsed and dried. On deep blond hair, there is obtained a light golden blond coloration. The combing of the hair, wet or dry, is easy. The hair thus treated is shiny, lively, easy to style and has body which lasts after several shampooings.

8c—A cream having the following formulation is prepared:

| | |
|---|---|
| Cetyl stearyl alcohol | 16 g |
| Oleic diethanolamide | 3 g |
| Sodium cetyl stearyl sulfate | 5 g |
| Compound $B_{17}$ | 2.5 g |
| Compound $A'_3$ | 4.5 g |
| Ammonia - 22° Bé | 10 ml |
| Paratoluylene diamine | 0.28 ml |
| Para amino phenol | 0.090 g |
| Meta diamino anisole sulfate | 0.05 g |
| Resorcinol | 0.250 g |
| Meta amino phenol base | 0.070 g |
| Trilon B | 1 g |
| Sodium bisulfite, d = 1.32 | 1.2 g |
| Water, sufficient for | 100 g |

30 g of this cream are mixed with 45 g of $H_2O_2$ (20 volumes), thereby providing a smooth cream which adheres well to the hair. This cream is permitted to remain in contact with the hair for 30-45 minutes, at which time the hair is then rinsed and dried. On chestnut colored, hair, there is obtained a light ash chestnut shade. The combing of the hair, wet or dry, is very easy. The hair thus treated is shiny, controlled and easy to set. The hair has body which lasts after several shampooings.

EXAMPLE 9—Shampoo Compositions

9a—An anionic shampoo having the following composition is prepared:

| | |
|---|---|
| Triethanolamine $C_{12}-C_{14}$ alkyl sulfate | 10 g |
| Hydroxypropylmethyl cellulose | 0.2 g |
| $C_{12}-C_{18}$ alkyl dimethyl ammoniacetate, sold under the name DEHYTON AB 30 | 8 g |
| Compound $A_8$ | 0.15 g |
| Compound $B_1$ | 0.20 g |
| Water, sufficient for | 100 g |
| pH - 7.2 (spontaneous) | |

This shampoo, in the form of a clear liquid, when applied to natural, permanent-waved hair, provides good untangling of the hair when wet. After drying, the hair is soft, shiny and lively.

9b—An anionic shampoo having the following composition is prepared:

| | |
|---|---|
| Triethanolamine $C_{12}-C_{14}$ alkyl sulfate | 10 g |
| Hydroxypropylmethyl cellulose | 0.2 g |
| Copra diethanolamide | 2 g |
| Compound $A_8$ | 0.5 g |
| Compound $B_1$ | 0.7 g |
| Water, sufficient for | 100 g |
| pH = 7.3 (spontaneous) | |

When applied to dyed hair, this slightly viscous, clear shampoo, facilitates untangling of the hair when wet. Dry hair thus treated is easy to comb; is soft and shiny; and is easy to style.

9c—An anionic shampoo having the following composition is prepared:

| | |
|---|---|
| Triethanolamine $C_{12}-C_{14}$ alkyl sulfate | 10 g |
| Hydroxypropylmethyl cellulose | 0.2 g |
| Compound $A_1$ | 0.75 g |
| Compound $B_1$ | 0.3 g |
| Water, sufficient for | 100 g |
| pH = 7.5 (spontaneous) | |

This shampoo, in the form of a clear liquid, when applied to natural permanent-waved hair, provides essentially the same favorable results outlined in Example 9a.

9d—An anionic shampoo having the following composition is prepared:

| | |
|---|---|
| Triethanolamine $C_{12}-C_{14}$ alkyl sulfate | 10 g |
| Hydroxypropylmethyl cellulose | 0.2 g |
| Compound $B_5$ | 0.5 g |
| Compound $A_8$ | 0.5 g |
| Water, sufficient for | 100 g |
| pH = 7 (spontaneous) | |

This shampoo, in the form of a clear liquid, when applied to dyed hair, facilitates combing the hair when wet and imparts to dry hair, thus treated, liveliness, fullness and a shiny appearance.

9e—A non-ionic shampoo having the following composition is prepared:

| | |
|---|---|
| $R-CHOH-CH_2O-(CH_2-CHOH-CH_2-O)_{n_2}H$ wherein R = $C_9-C_{12}$ alkyl and $n_2$ = 3.5 | 7 g |
| Lauryl alcohol polyoxyethylenated with 12 moles of ethylene oxide | 7 g |
| Lauric diethanolamide | 3 g |
| Compound $A_1$ | 0.5 g |
| Compound $B_1$ | 0.75 g |

| Water, sufficient for | 100 g |
|---|---|
| pH, adjusted to 6 with lactic acid | |

When applied to natural hair, this shampoo which is provided in the form of a clear liquid, facilitates the combing of wet hair. Dry hair, thus treated, is lively, full and shiny.

9f—A cationic shampoo having the following composition is prepared:

| Lauryl alcohol polyoxy-<br>ethylenated with 12 moles<br>of ethylene oxide | 5 g |
|---|---|
| $C_{12}$-$C_{18}$ alkyl dimethyl<br>ammoniacetate, sold under<br>the name DEHYTON AB 30 | 10 g |
| Copra diethanolamide | 3 g |
| Compound $A_1$ | 0.75 g |
| Compound $B_1$ | 0.25 g |
| Water, sufficient for | 100 g |
| pH, adjusted to 4 with lactic acid | |

This shampoo which is provided in the form of a clear liquid, when applied to dyed hair, provides excellent untangling of the wet hair and makes the hair very soft. Dry hair, thus treated, is shiny, soft and very controlled.

9g—A non-ionic shampoo having the following composition is prepared:

| R—CHOH—CH$_2$—O—(CH$_2$—CHOH—CH$_2$—O$)_{\overline{n_2}}$H<br>wherein R = C$_9$-C$_{12}$ alkyl<br>and $n_2$ = 3.5 | 10 g |
|---|---|
| Copra diethanolamide | 3 g |
| Compound $B_{16}$ | 0.5 g |
| Compound $A_1$ | 0.2 g |
| Water, sufficient for | 100 g |
| pH = 8.6 (spontaneous); adjusted to<br>pH 6 with lactic acid | |

This shampoo, provided in the form of a clear liquid, when applied to wet hair, facilitates the combing thereof. Dry hair, thus treated, is controlled and shiny.

9h—An anionic shampoo having the following composition is prepared:

| R—CHOH—CH$_2$—O—(CH$_2$CHOH—CH$_2$O$)_{\overline{n_2}}$H<br>wherein R = C$_9$-C$_{12}$<br>alkyl and $n_2$ = 3.5 | 10 g |
|---|---|
| Triethanolamine C$_{12}$-C$_{14}$<br>alkyl sulfate | 2 g |
| Copra diethanolamide | 3 g |
| Compound $B_{15}$ | 0.5 g |
| Compound $A_1$ | 0.1 g |
| Water, sufficient for | 100 g |
| Initial pH - 7.9, adjusted to<br>pH 6 with lactic acid | |

This shampoo, provided in the form of a slightly opalescent liquid, when applied to dyed hair, facilitates the combing of the wet hair and imparts softness thereto. Dry hair thus treated is lively and full.

9i—An anionic shampoo having the following composition is prepared:

| Carboxylated alcohol<br>ethoxylated with 10 moles<br>of ethylene oxide, sold | |
|---|---|
| under the name AKYPO RLM 100 | 3 g |
| Lauryl alcohol polyethoxylated<br>with 12 moles of<br>ethylene oxide | 7 g |
| Lauric diethanolamide | 3 g |
| Compound $B_{13}$ | 0.6 g |
| Compound $A_1$ | 0.3 g |
| Water, sufficient for | 100 g |
| Initial pH - 4.5, adjusted to<br>pH 7.2 with triethanolamine | |

This shampoo, provided in the form of a clear liquid, when applied to dyed hair, facilitates the combing of the hair when wet. Dry hair thus treated is shiny.

9j—A non-ionic shampoo having the following composition is prepared:

| R—CHOH—CH$_2$—O(CH$_2$—CHOH—CH$_2$—O$)_{\overline{n_2}}$H<br>wherein R = C$_9$-C$_{12}$ alkyl<br>and $n_2$ = 3.5 | 10 g |
|---|---|
| Copra diethanolamide | 2 g |
| Compound $B_{15}$ | 0.7 g |
| Compound $A_2$ | 0.3 |
| Water, sufficient for | 100 g |
| pH = 7 (spontaneous) | |

This shampoo, provided in the form of a clear liquid, when applied to natural permanent waved hair, facilitates the untangling of the hair when wet and imparts softness thereto. Dry hair, thus treated, is lively, full and easy to control.

9k—A non-ionic shampoo having the following composition is prepared:

| Compound $B_{19}$ | 0.5 g |
|---|---|
| Compound $A_1$ | 0.5 g |
| R—CHOH—CH$_2$—O—(CH$_2$—CHOH—CH$_2$—O$)_{\overline{n_2}}$H<br>wherein R = C$_9$-C$_{12}$ alkyl<br>and $n_2$ = 3.5 | 7 g |
| Lauryl alcohol polyoxyethylenated<br>with 12 moles of<br>ethylene oxide | 3 g |
| Copra diethanolamine | 3 g |
| Water, sufficient for | 100 g |
| pH = 7.8 (spontaneous) | |

When applied to natural hair, this shampoo which is provided in the form of a clear liquid, facilitates untangling the wet hair. Dry hair, thus treated, is shiny, lively and easy to style.

9l—A cationic shampoo having the following composition is prepared:

| $C_{12}$-$C_{18}$ alkyl dimethyl<br>ammoniacetate, sold under<br>the name DEHYTON AB 30 | 10 g |
|---|---|
| Lauryl alcohol polyoxyethylenated<br>with 12 moles of<br>ethylene oxide | 5 g |
| Lauric diethanolamide | 3 g |
| Compound $B_{14}$ | 0.8 g |
| Compound $A_1$ | 0.2 g |
| Perfume, Dye | |
| Water, sufficient for | 100 g |
| pH, adjusted to 6 | |

This shampoo, provided in the form of a clear liquid, when applied to the hair, assures good untangling of wet hair. Dry hair, thus treated, is controlled while having good liveliness.

9m—A non-ionic shampoo having the following composition is prepared:

| | |
|---|---|
| R—CHOH—CH$_2$—O—(CH$_2$—CHOH—CH$_2$—O)$_{\overline{n_2}}$H wherein R = C$_9$-C$_{12}$ alkyl and n$_2$ = 3.5 | 10 g |
| Copra diethanolamide | 3 g |
| Compound A$_1$ | 0.4 g |
| Compound B$_{20}$ | 0.7 g |
| Dye | |
| Water, sufficient for | 100 g |
| pH, adjusted to 6 | |

This clear liquid shampoo facilitates untangling wet hair. Dry hair, thus treated, is soft, shiny and easy to style.

EXAMPLE 10—Lotion For Use Before A Permanent Wave Treatment

The following composition is prepared:

| | |
|---|---|
| Compound B$_2$ | 1 g |
| Compound A$_2$ | 1.4 g |
| Trimethyl cetyl ammonium chloride | 0.2 g |
| Water, sufficient for | 100 g |
| pH, adjusted to 7 | |

This lotion is applied to natural hair and is permitted to remain in contact therewith for 5 minutes. Without rinsing off this lotion, a permanent wave composition is applied to the hair.

After fixation, the waves obtained are particularly beautiful. The hair is easy to style; is soft; and has body.

EXAMPLE 11—The following shampoo compositions are prepared:

11a

| | |
|---|---|
| Triethanolamine C$_{12}$-C$_{14}$ alkyl sulfate | 15 g |
| Hydroxypropylmethyl cellulose | 0.2 g |
| Lauric diethanolamide | 3 g |
| Compound A$_1$ | 0.4 g |
| Compound B$_{21}$ | 1 g |
| Perfume | 0.1 g |
| Dye | 0.1 g |
| Water, sufficient for | 100 g |

11b

| | |
|---|---|
| Triethanolamine C$_{12}$-C$_{14}$ alkyl sulfate | 10 g |
| Hydroxypropylmethyl cellulose | 0.3 g |
| Compound A$_8$ | 0.5 g |
| Compound B$_{22}$ | 0.5 g |
| Perfume | 0.1 g |
| Dye | 0.02 g |
| Water, sufficient for | 100 g |

What is claimed is:

1. A cosmetic composition in lotion, cream, gel or emulsion form for conditioning the hair comprising
   (1) in combination at least one crosslinked polyaminoamide and at least one cationic polymer having recurring units of the formula

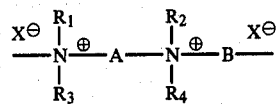

wherein
   R$_3$ and R$_4$ each independently represent alkyl having 1-3 carbon atoms,
   R$_1$ and R$_2$ each independently represent alkyl having 1-3 carbon atoms or hydroxyalkyl having 1-3 carbon atoms, or when R$_2$=R$_4$=CH$_3$ and R$_1$=R$_3$, R$_1$ and R$_3$ can represent alkyl having 4-8 carbon atoms, or when R$_2$=R$_4$=R$_1$=CH$_3$, R$_3$ can represent benzyl, cyclohexyl or alkyl having 4-12 carbon atoms,
   A and B, each independently, represent linear or branched alkylene having 2-20 carbon atoms in the chain, —(CH$_2$)$_n$—(CH$_2$)$_n$—, —CH$_2$—C$_6$H$_4$—CH$_2$— or —CH$_2$—CH(OH)—CH$_2$—, n being a whole number equal to 2 or 3,
   X$^\ominus$ is an anion and
   Z represents either —O— or —NH—CO—NH—, wherein said crosslinked polyamino-amide is present in an amount of 0.1 to 5 weight percent and said quaternized polymer is present in an amount of 0.1 to 10 weight percent, based on the total weight of said composition, and
   (2) an effective amount of at least one of (i)-(iv), defined below, to provide said lotion, cream, gel or emulsion:
      (i) water, alcohol or mixtures thereof;
      (ii) soap or C$_{12}$-C$_{18}$ natural or synthetic alcohols with emulsifiers;
      (iii) thickening agent; or
      (iv) mixtures of oils, waxes, or both with fatty alcohols and polyethoxylated fatty alcohols.

2. The composition of claim 1 wherein the crosslinked polyamino-amide is obtained by crosslinking a polyamino-amide resulting from the polycondensation of an acid derivative on a polyamine.

3. The composition of claim 2 wherein the acid derivative is selected from the group consisting of organic dicarboxylic acids, ethylenically unsaturated aliphatic mono- and di-carboxylic acids, the esters of said acids and mixtures thereof.

4. The composition of claim 3 wherein said organic dicarboxylic acid has 3–10 carbon atoms.

5. The composition of claim 4 wherein said organic dicarboxylic acid is selected from the group consisting of adipic acid, 2,2,4-trimethyl adipic acid, 2,4,4-trimethyl adipic acid, diglycolic acid and terephthalic acid.

6. The composition of claim 3 wherein said ethylenically unsaturated aliphatic mono- or di-carboxylic acid is selected from the group consisting of acrylic acid, methacrylic acid and itaconic acid.

7. The composition of claim 2 wherein said polyamino-amide is obtained from a polyamine which is a polyalkylene polyamine having both bis-primary and mono- or di-secondary amines.

8. The composition of claim 7 wherein said polyamine is selected from the group consisting of diethylenetriamine, dipropylenetriamine, triethylene tetramine and mixtures thereof.

9. The composition of claim 7 wherein the poly-condensation is carried out on a mixture of said polyalkylene polyamines having both bis-primary and mono- or di-secondary amines with a second polyamine, at a rate of 0 to 40 mole percent of the said second polyamine, said second polyamine being a bis-primary or bis-secondary amine.

10. The composition of claim 9 wherein said second polyamine is selected from the group consisting of ethylenediamine, hexamethylene diamine and piperazine.

11. The composition of claim 1 wherein said polyamino-amide is crosslinked by a crosslinking agent selected from the group consisting of:
(a) epihalohydrin, diepoxide, dianhydride, unsaturated anhydride, bis-unsaturated derivative, bis-halohydrin, bis-azetidinium, bis-haloacyl derivative of a diamine and alkyl bis-halide;
(b) oligomer obtained from the crosslinking agent in (a);
(c) quaternization product of the crosslinking agent in (a) and (b) having alkylatable tertiary amine groups.

12. The composition of claim 11 wherein said crosslinked polyamino-amide is obtained with 0.025 to 0.35 molecule of crosslinking agent per amine group of said polyamino-amide.

13. The composition of claim 12 wherein said crosslinked polyamino-amide is obtained with less than 0.2 molecule of crosslinking agent per amine group of said polyamino-amide.

14. The composition of claim 1 wherein said polyamino-amide is crosslinked by a crosslinking agent selected from the group consisting of:
(1) epichlorohydrin,
(2) diglycidyl ether,
(3) N,N'-bis-epoxypropyl piperazine,
(4) the dianhydride of butanetetracarboxylic acid,
(5) the dianhydride of pyromellic acid,
(6) divinyl sulfone,
(7) methylene bis-acrylamide,
(8) N,N'-bis-epoxypropyl piperazine quaternized with 1-2 moles of dimethyl sulfate,
(9) piperazine bis-acrylamide,
(10) bis-unsaturated oligomer obtained by the reaction of an excess of piperazine bis-acrylamide on piperazine,
(11) a bis-halohydrin oligomer obtained by the reaction of excess epichlorohydrin on piperazine,
(12) the oligomer of (11) quaternized with dimethyl sulfate,
(13) 1,3-bis-piperazinyl-2-propanol quaternized with epichlorohydrin,
(14) piperazine bis-chloracetamide,
(15) piperazine bis omega-bromo-undecanamide,
(16) a bifunctional alkylating agent of the formula

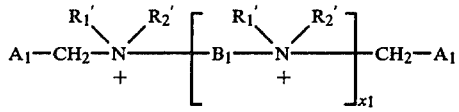

wherein
$x_1$ represents a whole number between 0 and 7,
$A_1$ represents

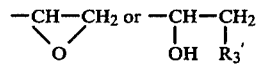

where $R'_3$ represents Cl or Br,
$R'_1$ and $R'_2$ each independently represent alkyl or hydroxyalkyl having 1-4 carbon atoms, and
$B_1$ represent alkylene having 2-6 carbon atoms,

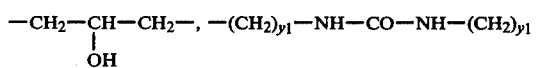

where $y_1$ is a whole number between 1 4 , and
(17) bis-epoxypropyl dimethyl ammonium bromide.

15. The composition of claim 1 in the form of a lotion.

16. The composition of claim 15 wherein said lotion contains a mixture of water and alcohol and said alcohol is ethanol or isopropanol.

17. The composition of claim 1 in the form of a cream, a gel or an emulsion

18. The composition of claim 1 which also contains from 0.2 to 2 weight percent of a phosphoric ester of a $C_{12}$-$C_{18}$ saturated or unsaturated fatty alcohol, oxyethylenated or not.

19. A process for conditioning the hair comprising applying to said hair an effective amount of the composition of claim 1.

* * * * *

UNITED STATES PATENT AND TRADEMARK OFFICE
CERTIFICATE OF CORRECTION

PATENT NO. : 4,201,766
DATED : May 6, 1980
INVENTOR(S) : Jean-Francois Grollier and Chantal Fourcadier It is certified that error appears in the above-identified patent and that said Letters Patent are hereby corrected as shown below:

Column 32, line 31, "between 1 4" should read

-- between 1 and 4 --

Signed and Sealed this

Ninth Day of December 1980

[SEAL]

Attest:

SIDNEY A. DIAMOND

Attesting Officer

Commissioner of Patents and Trademark